United States Patent [19]

Jackman

[11] Patent Number: 4,614,822

[45] Date of Patent: Sep. 30, 1986

[54] CATALYTIC OXIDATION OF 3,3-DIMETHYL-2-HYDROXYBUTYRIC ACID TO 2-OXO ACID AND PREPARATION OF 4-AMINO-6-TERT.-BUTYL-3-THIO-1,2,4-TRIAZINE-5(4-H)-ONE

[75] Inventor: Dennis E. Jackman, Prairie Village, Kans.

[73] Assignee: Mobay Chemical Corporation, Pittsburgh, Pa.

[21] Appl. No.: 181,542

[22] Filed: Aug. 26, 1980

Related U.S. Application Data

[63] Continuation of Ser. No. 960,330, Nov. 13, 1978, abandoned.

[51] Int. Cl.$^4$ .................. C07C 51/373; C07C 59/185; C07D 253/06
[52] U.S. Cl. ..................................... 544/182; 562/525; 562/577
[58] Field of Search .......................... 562/577; 544/182

[56] References Cited

U.S. PATENT DOCUMENTS

| | | | |
|---|---|---|---|
| 3,479,403 | 11/1969 | MacLean | 568/478 |
| 3,905,801 | 9/1975 | Fawzi | 71/93 |
| 4,052,460 | 10/1977 | Dickare | 562/577 |
| 4,113,767 | 9/1978 | Merz | 562/577 |

OTHER PUBLICATIONS

Rylander, Org. Syn. with Noble Metal Catalysts, V. 28 (1973) pp. 133–134.

*Primary Examiner*—Vivian Garner
*Attorney, Agent, or Firm*—Sprung Horn Kramer & Woods

[57] ABSTRACT

Sodium 3,3-dimethyl-2-hydroxybutyrate and ruthenium dioxide hydrate are added to water, the pH rendered alkaline, and sodium hypochlorite is slowly added to produce sodium 3,3-dimethyl-2-oxobutyrate in high yield and purity. The solid catalyst is filtered off and may be re-used while the filtrate can be directly used in further synthesis.

8 Claims, No Drawings

CATALYTIC OXIDATION OF 3,3-DIMETHYL-2-HYDROXYBUTYRIC ACID TO 2-OXO ACID AND PREPARATION OF 4-AMINO-6-TERT.-BUTYL-3-THIO-1,2,4-TRIAZINE-5(4-H)-ONE

This is a continuation of application Ser. No. 960,330, filed Nov. 13, 1978, abandoned.

The present invention relates to the preparation of 3,3-dimethyl-2-oxobutyric acid and its salts.

U.S. Pat. No. 3,905,801 discloses the condensation of α-oxo-alkanoic acids with thiocarbohydrazide to produce 4-amino-6-(substituted)-3-thio-1,2,4-triazin-5(4-H)-ones which can be methylated to give 4-amino-6-(substituted)-3-(methylthio)-1,2,4-triazin-5-(4-H)-ones of which the 6-tert.butyl derivative is an especially effective selective herbicide of special utility in the cultivation of soybeans, tomatoes, potatoes, and the like. It is disclosed in that patent that 2-oxoacids can be prepared from the 2-hydroxy counterparts by oxidation with potassium permanganate.

This process is quite acceptable and has been used successfully in making millions of pounds of the 6-tert.butyl derivative but it has not inexpensive due to the high cost of potassium permanganate. In addition, it results in large quantities of by-product manganese dioxide which must be disposed of, with possible environmental impact.

It is accordingly an object of the present invention to provide an improved process for the preparation of 3,3-dimethyl-2-oxobutyric acid and/or its salts.

These and other objects and advantages are realized in accordance with the present invention pursuant to which a salt of 3,3-dimethyl-2-oxobutyric acid is prepared by reacting 3,3-dimethyl-2-hydroxybutyric acid with a hypochlorous salt under alkaline conditions in the presence of ruthenium as catalyst.

Advantageously the salts are sodium salts although other alkali metal and alkaline earth metal salts can be used provided they are soluble in the reaction medium, e.g. water.

The reaction medium is preferably of a pH of about 9 to 13, especially about 10 to 12. Since some hydroxyl ion appears to be consumed during the reaction, either it is initially supplied in excess or alkali is added during oxidation to maintain the desired pH. If the pH of the hydroxy salt solution is below about 6.0 or if the free caustic content of the hypochlorite solution is lowered to below about 1.3%, the desired oxidation does not proceed to any significant extent and further addition of hypochlorite merely cleaves any keto acid which may be present. In addition, the Ru catalyst is converted to a water soluble form which is difficult to recover from the solution.

The hypochlorite is advantageously used in excess to ensure complete conversion of the 2-hydroxyacid using about 5 to 15% excess. The hypochlorite can be formed in situ, e.g. by bubbling chlorine gas into an aqueous caustic solution of the hydroxy acid containing the catalyst.

The reaction proceeds even at room temperature but preferably is conducted at about 40° C. or higher to speed it up. Above about 60° C. pivalic acid is produced so advantageously the oxidation is carried out at or below 60° C.

The ruthenium catalyst is oxidized by the hypochlorite to produce a mixture of ruthenate, perruthenate and ruthenium tetroxide, the ruthenate predominating. At the end of the reaction the ruthenium oxide is an insoluble solid present in substantially the same amount as initially so it can be filtered off and reused, even without treatment, in another cycle. The ruthenium can be supplied to the reaction solution in the form of a salt or an oxide, ruthenium dioxide and especially ruthenium dioxide hydrate being preferred. The oxide, for example, could be formed in situ commencing with a salt such as ruthenium trichloride.

The ruthenium oxide is employed in catalytic amounts, e.g. from between 0.01 g to about 1.0 g per mole of hydroxyacid, preferably between about 0.1 g to 0.5 g per mole.

The catalyst and hydroxacid salt aqueous solution is adjusted to the desired pH and the temperature brought to the desired value. Then caustic soda and chlorine or pre-formed NaOCl can be added dropwise or incrementally. After all the oxidizing agent is added the mass is maintained to ensure completion of the reaction and then it is filtered to separate the catalyst from the solution containing the product in high yield and purity.

The oxidation proceeds rapidly and addition of the hypochlorite within only 5 minutes results in very high yields. Advantageously, somewhat longer reaction times are employed, e.g. about 30 minutes or an hour, to permit the ruthenium catalyst to be returned to suitable insoluble form for filtration and then re-use in a further cycle. The resulting solution can then be used directly for reaction with thiocarbohydrazide to form 4-amino-6-(tert-butyl)-3-thio-1,2,4-triazin-5(4-H)-one.

In Chemical Communications 1420 (1970) it is taught that compounds containing the grouping —CHOH—CO— undergo carbon-carbon cleavage under ruthenium-catalyzed oxidation rather than conversion to —CO—CO—, e.g.

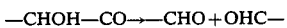

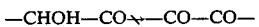

Surprisingly, however, with the instant starting materials and conditions of alkalinity oxidation proceeds herein by conversion of the hydroxy group to a carbonyl without cleavage between the hydroxy-bearing and carbonyl-bearing carbon atoms.

The invention will be further described in the following illustrative examples wherein all parts are by weight unless otherwise expressed:

EXAMPLE 1

(a) A 2 liter Morton flask equipped with a mechanical stirrer, thermometer, condenser, and dropping funnel was charged with 559 g of an 11.8% aqueous solution of 3,3-dimethyl-2-hydroxybutyric acid ("hydroxy acid") as the sodium salt (0.5 mole) and 0.2 g of ruthenium dioxide hydrate ($RuO_2.H_2O$). The pH was raised to 12 and the temperature to 40° C. With rapid stirring, 330.5 g of 12.1% NaOCl (0.5 mole+7.5% excess) in water was added dropwise over about ½ hour while the temperature was maintained at 40° C. with an ice bath. When the addition was complete the ice bath was removed and the solution was stirred for one hour, then filtered to remove catalyst to give 879 g of a 7.5% aqueous solution of 3,3-dimethyl-2-oxobutyric acid ("keto acid") as the sodium salt; approximate yield 100%.

(b) At the end of the oxidation the Ru catalyst was in the form of the black, water-insoluble ruthenium dioxide hydrate. It was removed by filtration employing Celite filter aid. The wet filter cake of catalyst plus filter aid was added directly into a further batch of hydroxy acid salt solution and another oxidation conducted as before by addition of hypochlorite.

(c) To 956 g of a 15.8% thiocarbohydrazide solution in dilute HCl at 70° there were added over a 10-minute period 2682 g of 7.27% keto acid filtrate produced as in (a) (temperature=70° C.) with rapid stirring. After heating at 70° C. (pH 1.3) for 4 hours the solution was cooled to room temperature and filtered. The solid was washed with water and air dried to give 272.2 g of 99.3% pure 4-amino-6-tert.-butyl-3-thio-1,2,4-triazin-5(4-$\underline{H}$)-one.

EXAMPLE 2

A 1 liter 4-neck round bottom flask equipped with a stirrer, thermometer, and addition funnel was charged with 524 g of aqueous solution containing 0.5 mole of "hydroxy acid" and 100 mg of ruthenium dioxide hydrate. The temperature was held at 15° C. with an ice bath and stirred while 294 g of 11.9% NaOCl solution was added dropwise over about 1.5 hours. The solution was then stirred for one hour while it was allowed to come to room temperature. Filtration through GFA glass fiber filter paper and washing the $RuO_2$ with a small amount of dilute caustic gave 829 g of 7.25% keto acid. Notwithstanding the low temperature and small amount of catalyst, the yield was 94.4%.

EXAMPLE 3

The reaction was run as Example 1 except that the temperature was kept at 80° C. Thus, 427.4 g (3.5% excess) of 9.0% NaOCl was added over about ½ hour to 555 g of 11.7% "hydroxy acid" containing 0.4 g of $Ru_2.H_2O$. Filtration gave 982 g of product containing 5.82% "keto acid" (87.9%), 0.44% unreacted "hydroxy acid" (6.5%), and 0.32% (6.6% yield) of pivalic acid, as salt. Thus, the higher temperature results in small amounts of undesired pivalic acid by-product.

EXAMPLE 4

As in Example 1, the NaOCl was added at a constant rate over 5 minutes while the temperature of the reaction mixture was kept at 40° C. This gave 982 g of product with 6.36% keto (96.1% yield) and no unreacted "hydroxy acid". 0.3 g of $Ru_2.H_2O$ was used. The lower temperature avoided pivalic acid formation but the faster addition, compared with Example 1, resulted in a small drop in yield.

EXAMPLE 5

Repeating Example 4 except that the NaOCl solution was added over two hours, gave 983 g of product of which 6.55% was "keto acid" (yield 99%).

EXAMPLE 6

Example 1 was re-run using glass and platinum electrodes attached to a Sargent-Welch Model LS pH meter and a 10 mv recorder. The NaOCl was added at a constant rate with a metering pump. The potential of the solution was kept at 330–400 mv. Near the end of the reaction the reading climbed up to 500 mv at which point the NaOCl addition was stopped. There was obtained from 559 g of 11.8% hydroxy acid solution 921 g of 6.7% "keto acid", yield 95%.

EXAMPLE 7

To a mixture of 120 ml of water, 100 ml of 50% sodium hydroxide solution, 1 g of $RuO_2$ hydrate, and 0.5 mole of "hydroxy acid" (559.3 g of an 11.8% solution) was added chlorine gas at about 0.5 g/min. The temperature was maintained at 0°–5° C. and when approximately 0.7 moles of $Cl_2$ had been added the solution was allowed to warm to room temperature and was filtered to give 839 g of product containing 7.05% keto acid (91% yield) and 0.38% hydroxy acid (4.8% yield).

EXAMPLE 8

As in Example 1 except ruthenium trichloride hydrate was used. 350.5 g of 11.4% NaOCl was added dropwise to a solution of 511.6 g of 12.9% hydroxy acid containing 0.3 g of $RuCl_3:H_2O$. This gave 818.7 g of 7.25% keto acid solution with a yield of 91.3%.

EXAMPLE 9

As in Example 1 279.7 g of 11.8% hydroxy acid was charged to the flask and the pH was adjusted to 12. 0.3 g of $RuO_2.H_2O$ was added and 76.8 g of 26% NaOCl solution was added dropwise. This gave 341 g of 9.53% keto acid solution with a yield of 100%.

It will be appreciated that the instant specification and examples are set forth by way of illustration and not limitation, and that various modifications and changes may be made without departing from the spirit and scope of the present invention.

What is claimed is:

1. A process for the preparation of a salt of 3,3-dimethyl-2-oxo-butyric acid comprising reacting 3,3-dimethyl-2-hydroxybutyric acid with a hypochlorous acid salt under alkaline conditions in the presence of ruthenium as catalyst.

2. A process according to claim 1, wherein the salt of 3,3-dimethyl-2-hydroxybutyric acid and the ruthenium are first combined in water, and the hypochlorous acid salt is then added to the water in at least stoichiometric amount.

3. A process according to claim 1, wherein the ruthenium is employed in the form of ruthenium dioxide hydrate or ruthenium trichloride hydrate.

4. A process according to claim 1, wherein the salt of 3,3-dimethyl-2-hydroxybutyric acid is the sodium salt, and the hypochlorous acid salt is the sodium salt.

5. A process according to claim 4, wherein the sodium 3,3-dimethyl-2-hydroxybutyric acid is first added to water along with ruthenium in the form of ruthenium dioxide hydrate, the pH is maintained between about 9 and 13, the temperature is maintained between about 40° and 60° C., sodium hypochlorite is added to the water in at least stoichiometric amount, and the solution is thereafter filtered to separate the catalyst from the solution containing sodium 3,3-dimethyl-2-oxobutyrate.

6. A process according to claim 5, wherein the filtered off ruthenium catalyst is directly employed in oxidation of another quantity of 3,3-dimethyl-2-hydroxybutyric acid.

7. A process according to claim 1, wherein the hypochlorous acid salt is formed in situ by addition of caustic and chlorine gas.

8. In the production of 4-amino-6-tert.-butyl-3-thio-1,2,4-triazin-5(4-H)-one by oxidizing 3,3-dimethyl-2-hydroxybutyric acid to 3,3-dimethyl-2-oxo-butyric acid and condensing the 3,3-dimethyl-2-oxo-butyric acid with thiocarbohydrazide, the improvement which comprises effecting the oxidation by adding sodium 3,3-dimethyl-2-hydroxybutyric acid to water along with ruthenium dioxide hydrate, maintaining the pH between about 10 and 13, maintaining the temperature between about 40° and 60° C., adding sodium hypochlorite to the water in at least stoichiometric amount, filtering the solution to separate the catalyst from the solution containing sodium 3,3-dimethyl-2-oxobutyrate, and directly condensing the solution with thiocarbohydrazide.

* * * * *